United States Patent
Jimeno et al.

(10) Patent No.: US 9,545,418 B2
(45) Date of Patent: *Jan. 17, 2017

(54) ON01910.NA ENHANCES CHEMOTHERAPEUTIC AGENT ACTIVITY IN DRUG-RESISTANT TUMORS

(71) Applicant: THE JOHNS HOPKINS UNIVERSITY, Baltimore, MD (US)

(72) Inventors: Antonio Jimeno, Englewood, CO (US); Manuel Medina Hidalgo, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/624,057

(22) Filed: Feb. 17, 2015

(65) Prior Publication Data

US 2015/0209381 A1    Jul. 30, 2015

Related U.S. Application Data

(63) Continuation of application No. 12/988,471, filed as application No. PCT/US2008/005104 on Apr. 17, 2008, now Pat. No. 8,962,614.

(51) Int. Cl.
| | |
|---|---|
| *A61K 45/06* | (2006.01) |
| *A61P 35/00* | (2006.01) |
| *A61K 31/7076* | (2006.01) |
| *A61K 31/192* | (2006.01) |
| *A61K 31/713* | (2006.01) |
| *A61K 31/198* | (2006.01) |
| *A61K 31/7068* | (2006.01) |

(52) U.S. Cl.
CPC ......... *A61K 31/7076* (2013.01); *A61K 31/192* (2013.01); *A61K 31/198* (2013.01); *A61K 31/7068* (2013.01); *A61K 31/713* (2013.01)

(58) Field of Classification Search
USPC ... 435/6.1, 91.1, 455, 6; 424/9.1, 9.2; 514/1, 514/2, 44, 221, 274; 536/23.1
See application file for complete search history.

(56) References Cited

U.S. PATENT DOCUMENTS 8,962,614 B2 *   2/2015   Jimeno ............... A61K 31/192
                                                        424/9.1

* cited by examiner

*Primary Examiner* — Jane Zara
(74) *Attorney, Agent, or Firm* — John Hopkins Technology Transfer (57) ABSTRACT

The invention includes compositions and methods of treatment of cancers susceptible to treatment with nucleotide analog chemotherapeutic agent, including cancers in which nucleotide analog resistant tumors have developed, including identifying a subject having cancer susceptible to treatment with a nucleotide analog chemotherapeutic agent and a mitotic disruptor/polo-like kinase (Plk) pathway inhibitor to a subject; and monitoring the subject for a reduction of stabilization of at least one sign or symptom of cancer.

20 Claims, 5 Drawing Sheets

Fludarabine phosphate    Cladribine    Clofarabine

Gemcitabine    Ara-C    Decitabine

Sapacitabine    Capecitabine    Flurouracil

FIGURE 3B (cont'd)

Floxuridine

Pentostatin

Tioguanine

Mercaptopurine

ON01910.NA ENHANCES CHEMOTHERAPEUTIC AGENT ACTIVITY IN DRUG-RESISTANT TUMORS

CROSS-REFERENCE TO RELATED APPLICATIONS

This application is a continuation application of U.S. patent application Ser. No. 12/988,471, filed May 3, 2011, now U.S. Pat. No. 8,962,614, which is a 35 U.S.C. §371 U.S. national entry of International Application PCT/US2008/005104, having an international filing date of Apr. 17, 2008, the content of each of the aforementioned applications is herein incorporated by reference in their entirety.

BACKGROUND OF THE INVENTION

Broad range anti-cancer chemotherapeutic agents frequently act by inhibiting proliferation by disrupting cell division or inhibiting apoptosis in relatively rapidly dividing cells. One strategy is to inhibit cell proliferation is to use nucleotide analog chemotherapeutic agents such as cladribine, clofarabine, fludarabine, mercaptopurine, pentostatin, thioguanine, capecitabine, cytarabine, decitabine, fluorouracil, floxuridine, sapacitabine, and gemcitabine. The compounds are structurally similar and typically act by at least interfering with DNA replication. Nucleotide analog chemotherapeutic agents are used to treat, or are under study for treatment of, a variety of cancers including hematological malignancies such as leukemia and lymphoma, colorectal cancer, pancreatic cancer, lung cancer, breast cancer, ovarian cancer, basal cell carcinoma, bladder cancer, hepatic cancer, prostate cancer, gastric cancer, renal cancer, melanoma, glioma, esophageal cancer, cervical cancer, and myelodysplastic syndromes.

Treatment with chemotherapeutic agents frequently results in the development of resistance to one or more chemotherapeutic drugs by various mechanisms. For example, gemcitabine resistance in cancer is a widespread problem. A large proportion of cancer patients end up receiving gemcitabine at some point of their care as is approved in lung, pancreatic, bladder, breast, and ovarian cancer, and is being investigated for the treatment of at least hepatic and esophageal cancer and is used for the treatment of lymphomas and other cancers experimentally. Although efficacious in a third of the cases for which the drug is approved, most do not respond, and even those who respond eventually develop resistance.

Gemcitabine resistance is particularly problematic in pancreatic cancer for which there are not other proven chemotherapeutic regimens. Despite advances in treatment of many types of cancer, pancreatic cancer remains difficult to treat with low long term survival. In 2004 the estimated incidence of the disease in the USA is 31,860 with an expected 31,270 deaths. One of the limitations of new drug development is the lack of appropriate preclinical models.

Overall, about 5% of patients with cancer of the exocrine pancreas will be alive 5 years after the cancer is found. Even for those with local disease, the 5-year relative survival rate is about 20%. For those who have regional disease, the 5-year relative survival rate is about 8%. If there are metastases, the 5-year relative survival rate is 2%. Although gemcitabine is approved for treatment for pancreatic cancer patients, about 75% to 90% of patients have minimal benefit from this therapy. No evidence-based treatment recommendation can be given for patients with advanced pancreatic cancer after failure of first line gemcitabine treatment.

Over the last few years, a significant number of clinical trials have explored the activity of new agents in pancreatic cancer alone or in combination with gemcitabine. The results of these studies have been mostly negative. Despite activity data in phase II studies, no single agent or combination strategy has been superior to gemcitabine alone in studies conducted thus far. This applies not only to conventional drugs but also to targeted agents such as matrix metalloproteinase (MMP) and farnesyl-transferase inhibitors (FTI).

Studies have been performed to identify appropriate treatments for pancreatic cancer patients who have failed gemcitabine therapy, but the results have been mixed. In one study, treatment consisted of docetaxel 65 mg/m$^2$ and irinotecan 160 mg/m$^2$, both administered every 21 days. Fourteen patients were enrolled before the study was closed due to excess toxicity. The most common grade 3/4 toxicities included neutropenia/leukopenia, nausea and vomiting, and diarrhea. Fully half of patients received only 1 treatment cycle, with a median time to treatment failure of 36 days. No objective responses were observed, although 3 patients had stable disease for at least 6 cycles. Overall survival for the entire cohort was 134 days, with a 6-month survival rate of 36%. In another study, patients with gemcitabine-resistant pancreatic cancer were treated with S-1 plus cisplatin (CDDP) to determine response rate and toxicity. Five of seventeen patients enrolled (29.4%) achieved a partial response and 2 (11.8%) had stable disease. Toxicities of the treatment were acceptable. The median survival time was 10 months (range, 20 months), with 63.7% and 31.9% of patients alive at 6 and 12 months, respectively.

SUMMARY OF THE INVENTION

In one aspect, the instant invention provides a method for the use of mitotic disruptor/polo-like kinase (Plk) pathway inhibitor, as a medicament for treatment of cancer in subjects with a cancer susceptible to treatment with a nucleotide analog chemotherapeutic agent. Such subjects include subjects in whom cancers were initially susceptible to treatment with nucleotide analog chemotherapeutic agents who later fail chemotherapy due to the development of resistance to nucleotide chemotherapeutic agents (i.e., develop a resistant tumor). The method of use includes preparation of a mitotic disruptor/Plk pathway inhibitor as a medicament for administration to the subject identified as having a type of cancer that is susceptible to treatment with a nucleotide analog chemotherapeutic agent, susceptible to treatment with a mitotic disruptor/Plk pathway inhibitor. In some embodiments, the subject has resistance or has developed resistance to nucleotide analog a chemotherapeutic agent. The method further includes monitoring the subject for reduction or stabilization of at least one sign or symptom of cancer wherein the medicament results in the reduction or stabilization of at least one sign or symptom of cancer. In an embodiment, the mitotic disruptor/Plk pathway inhibitor is co-administered with the nucleotide analog chemotherapeutic agent. In an aspect, the method for use includes reversing nucleotide analog chemotherapeutic agent resistance.

In one aspect, the instant invention provides a method for use of a mitotic disruptor/Plk pathway inhibitor for the preparation of a medicament for treatment of cancer in a subject with cancer who has been previously administered nucleotide analog chemotherapeutic agent alone, wherein the medicament is prepared for co-administration of a nucleotide analog chemotherapeutic agent and the subject is susceptible to treatment with a combination of a nucleotide analog chemotherapeutic agent and a mitotic disruptor/Plk pathway inhibitor. The method further includes monitoring the subject for reduction or stabilization at least one sign or symptom of cancer. In an aspect, the method includes preventing the development of nucleotide analog chemotherapeutic agent resistance.

In an aspect, the instant invention provides a method for the use of a mitotic disruptor/Plk pathway inhibitor for the preparation of a medicament for the treatment of cancer in a subject susceptible to treatment of cancer using a nucleotide analog chemotherapeutic agent. The method includes preparation of a medicament including a mitotic disruptor/Plk pathway inhibitor to be administered prior to a medicament including a nucleotide analog chemotherapeutic agent, optionally with continued administration of a mitotic disruptor/Plk pathway inhibitor, and monitoring the subject for reduction or stabilization at least one sign or symptom of cancer. In an aspect, the method for use of the medicaments includes preventing nucleotide analog chemotherapeutic agent resistance in a subject.

In an aspect, the invention includes co-administration of a nucleotide analog chemotherapeutic agent and a mitotic disruptor/Plk pathway inhibitor to produce a synergistic effect of the compounds such that the effect of co-administration of the compounds is greater than the additive effect of the compounds administered singly. In an aspect the invention includes preparation of a synergistic composition for use as a medicament for the treatment of cancer including a nucleotide analog chemotherapeutic agent and a mitotic disruptor/Plk pathway inhibitor.

In an aspect, the invention includes a regimen for administration of a nucleotide analog chemotherapeutic agent and a mitotic disruptor/Plk pathway inhibitor to a subject having a cancer susceptible to treatment with a nucleotide analog chemotherapeutic agent and/or a mitotic disruptor/Plk pathway inhibitor. In an embodiment, the regimen includes administration of a nucleotide analog chemotherapeutic agent alone, followed by co-administration of a nucleotide analog chemotherapeutic agent and a mitotic disruptor/Plk pathway inhibitor. In an embodiment, the regimen includes administration of a mitotic disruptor/Plk pathway inhibitor followed by co-administration of a mitotic disruptor/Plk pathway inhibitor with a nucleotide analog chemotherapeutic agent. In an embodiment, the regiment includes co-administration of a Plk inhibitor with a nucleotide analog chemotherapeutic agent, optionally without prior single administration of either agent alone. In an aspect, the invention optionally includes further administration of additional chemotherapeutic and/or pharmaceutical agents. In an aspect, the invention optionally further includes administration of a chemotherapeutic agent or a mitotic disruptor/Plk pathway inhibitor singly after co-administration of the two agents.

In an aspect, the invention includes preparation of a medicament including a mitotic disruptor/Plk pathway inhibitor for co-administration with a nucleotide analog chemotherapeutic agent for the treatment of a nucleotide analog chemotherapeutic agent resistant cancer in a patient susceptible to treatment with the medicament.

In an aspect, the invention includes preparation of a medicament including a mitotic disruptor/Plk pathway inhibitor for co-administration with a nucleotide analog chemotherapeutic agent for the prevention of the development of nucleotide analog chemotherapeutic agent resistant in cancer in a patient susceptible to treatment with the medicament.

In an aspect, the invention includes preparation of a medicament including a mitotic disruptor/Plk pathway inhibitor for co-administration with a nucleotide analog chemotherapeutic agent for use for the reversal of nucleotide analog chemotherapeutic agent resistance in cancer in a patient previously susceptible to treatment with the mitotic disruptor/Plk pathway inhibitor medicament.

In an embodiment the invention includes, a medicament for co-administration of a mitotic disruptor/Plk pathway inhibitor and nucleotide analog chemotherapeutic agent which is an admixture including a mitotic disruptor/Plk pathway inhibitor and a nucleotide analog chemotherapeutic agent. In an embodiment, a medicament for co-administration of a mitotic disruptor/Plk pathway inhibitor and a nucleotide analog chemotherapeutic agent includes preparation of each nucleotide analog chemotherapeutic agent and a mitotic disruptor/Plk pathway inhibitor in a dosage form to allow or facilitate administration of both compounds to a subject. In embodiments of the invention, the cancer is a cancer susceptible to treatment with a nucleotide analog therapeutic agent. In embodiments of the invention the cancer is a hematological malignancy such as leukemia and lymphoma, colorectal cancer, pancreatic cancer, lung cancer, breast cancer, ovarian cancer, basal cell carcinoma, bladder cancer, hepatic cancer, prostate cancer, gastric cancer, renal cancer, melanoma, glioma, esophageal cancer, cervical cancer, and myelodysplastic syndromes.

In various embodiments, the mitotic disruptor/Plk pathway inhibitor is a Plk1 inhibitor. In various embodiments, the mitotic disruptor/Plk pathway inhibitor is ON-01910-Na or a derivative thereof. In embodiments of the invention, the mitotic disruptor/Plk pathway inhibitor is ON-01910-Na. In various embodiments, the mitotic disruptor/Plk pathway inhibitor is a nucleic acid therapeutic. In various embodiments, the nucleic acid therapeutic is targeted to Plk1, specifically human Plk1. In various embodiments, the nucleic acid therapeutic is an siRNA compound.

In various embodiments of the invention, the nucleotide analog chemotherapeutic agent is cladribine, clofarabine, fludarabine, mercaptopurine, pentostatin, thioguanine, capecitabine, cytarabine, decitabine, fluorouracil, floxuridine, sapacitabine, or gemcitabine. In various embodiments, the nucleotide analog chemotherapeutic agent is gemcitabine.

BRIEF DESCRIPTION OF THE FIGURES

FIGS. 2A-2B shows results from in vivo experiments in mice with gemcitabine sensitive and resistant tumors. (2A) shows tumor growth plots of the three in vivo experiments. Tumor-bearing mice were distributed in 4 groups that were treated with vehicle, gemcitabine, ON 01910.Na and the combination of both agents (at full doses). (2B) is a bar graph of 2A. Error bars represent standard deviation.

DETAILED DESCRIPTION OF THE INVENTION

The present invention is based, at least in part, on the finding that gemcitabine sensitive tumors have reduced expression of Plk1, and that gemcitabine-resistant tumors are susceptible to treatment with mitotic disruptor/Plk pathway inhibitors, including ON-01910-Na and an siRNA compound directed to human Plk1. Moreover, inhibition of Plk1 in gemcitabine resistant tumors confers gemcitabine resistance to the previously resistant tumor. This susceptibility of gemcitabine resistant tumors to killing by Plk1 inhibitors was determined using gemcitabine pancreatic tumor resistant cell lines in vitro, human gemcitabine resistant pancreatic tumors ex vivo, and mouse xenograft model (i.e., in vivo).

ON-01910-Na is a small molecule that disrupts G2/M cell cycle transition and induces mitotic arrest of tumor cells characterized by spindle abnormalities leading to their apoptosis. This effect is at least partially related to its activity as a Plk1 inhibitor. As demonstrated herein, ON 01910 had activity in in vitro and in vivo models of gemcitabine resistant pancreatic cancer.

The term "treated," "treating" or "treatment" includes the diminishment or alleviation of at least one symptom associated or caused by the state, disorder or disease being treated. For example, treatment can be diminishment of one or several symptoms of a disorder or complete eradication of a disorder. Treatment can include an objective response of CR, PR, or SD as outlined in the table below.

Response of solid tumors to treatment can be characterized, for example, using World Health Organization (WHO) criteria or using the Responsive Evaluation Criteria in Solid Tumors Group (RECIST) unidimensional measurement guidelines. The criteria are set forth in the table below:

|  | WHO | RECIST |
|---|---|---|
| Measurability | Measurable, bidimensional | Measurable, unidimensional; conventional method ≥ 20 mm; Spiral CT ≥ 10 mm; Target vs non-target lesion |
|  | Non-measurable/ evaluable | Non-measurable |
| Objective response |  |  |
| Complete Response (CR) | Disappearance of all known lesion(s); confirmed at 4 weeks | Disappearance of all known lesion(s); confirmed at 4 weeks |
| Partial Response (PR) | At least 50% decrease; confirmed at 4 weeks | At least 30% decrease; confirmed at 4 weeks |
| Stable Disease (SD) | Neither PR nor PD criteria met | Neither PR nor PD criteria met |
| Progressive Disease (PD) | 25% increase; no CR, PR, or SD documented before increased disease, or new lesion(s) | 20% increase; no CR, PR, or SD documented before increased disease, or new lesion(s) |

See also Park et al., Measuring response in solid tumors: Comparison of RECIST and WHO response criteria. *Jpn. J. Clin. Oncolo.* 33:533-537, 2003, incorporated herein by reference. The unidimensional measurement in the RECIST criteria include measurement of only the longest diameter of all target lesions.

The term "drug resistant tumor" or "drug resistant cancer" and the like are understood as a tumor or cancer in which progressive disease (PD) criteria are met in the presence or upon administration of the drug. In culture, a resistant cell is understood as a cell that continues to grow in the presence of the drug. The growth rate is at least 5%, 10%, 20%, 30%, 40%, 50%, 60%, 70%, 80% relative to an untreated control cell in culture. Drug resistance can be resistance to a single, specific drug, or resistance to multiple drugs as is common in tumors expressing the multi-drug resistance gene (MDR).

A "tumor susceptible to treatment with a drug" or a "cancer susceptible to treatment with a drug" and the like are understood as a tumor or cancer in which CR, PR, or SD criteria are met in the presence or upon administration of the drug. In cell culture, a susceptible cell is a cell that stops growing/dividing or dies in response to treatment with a drug. A cancer susceptible to treatment can also be understood as a type of cancer susceptible to treatment, e.g., a type of cancer approved for treatment with a nucleotide analog chemotherapeutic agent, or a type of cancer in which benefit was derived for the treatment of that cancer in a study. For example, types of cancer susceptible to treatment with a nucleotide analog therapeutic agent include, but are not limited to, hematological malignancies such as leukemia and lymphoma, colorectal cancer, pancreatic cancer, lung cancer, breast cancer, ovarian cancer, basal cell carcinoma, bladder cancer, hepatic cancer, prostate cancer, gastric cancer, renal cancer, melanoma, glioma, esophageal cancer, cervical cancer, and myelodysplastic syndromes.

A cancer susceptible to treatment with a drug can become a cancer resistant to a drug, frequently in response to treatment with a drug.

The term "subject" is intended to include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from cancer. A human subject can be referred to as a patient.

The term "cancer" includes malignancies characterized by deregulated or uncontrolled cell growth, for instance carcinomas, sarcomas, leukemias, and lymphomas. Cancer includes solid tumors and non-solid tumors. Cancer includes cancer of any organ, including the pancreas. The term "cancer" includes primary malignant tumors, e.g., those whose cells have not migrated to sites in the subject's body other than the site of the original tumor, and secondary malignant tumors, e.g., those arising from metastasis, the migration of tumor cells to secondary sites that are different from the site of the original tumor.

The language "therapeutically effective amount" of a compound as used herein is the amount of the compound necessary or sufficient to result in CR, PR, or SD when administered to a subject as described herein. It is understood a that a therapeutically effective amount of each nucleotide analog chemotherapeutic agent and a mitotic disruptor/Plk pathway inhibitor for use in combination with each other may not be sufficient to be effective when used alone. Compounds that have a therapeutic effect can be referred to as drugs or pharmaceutical agents.

The phrase "synergistic combination" includes combinations of therapeutic agents wherein the therapeutic result of administration of the combination of drugs is greater than the additive effect than would be expected for the drug combination. For example, in cells or tumors that are gemcitabine resistant (i.e., gemcitabine treatment does not induce CR, PR, or SD, i.e., has no effect), the administration of a combination of gemcitabine and a mitotic disruptor/Plk pathway inhibitor has a larger therapeutic effect than administration of the mitotic disruptor/Plk pathway inhibitor alone.

The phrase "co-administration" is understood herein as administration of two or more drugs to a subject for treatment of a single disease or condition, such as cancer, such that the two drugs are present and/or have activity in the subject at the same time. Co-administration includes both preparation of an admixture of the drugs to be administered together, preparation or formulation of drugs in specific carriers or at specific concentrations to facilitate mixture and/or sequential administration. Drugs can be packaged together in the same vial or bottle; or in separate bottles or vials in a single container (e.g. a box). The drugs need not be formulated specifically to be administered together. It is understood that different drugs have different pharmacokinetic and pharmacodynamic properties such that administration schedules can vary substantially. Therefore, simultaneous administration is not required. Co-administration of a nucleotide analog chemotherapeutic agent and a mitotic disruptor/Plk pathway inhibitor does not preclude administration of other chemotherapeutic agents or other drugs. Example regimens for co-administration are provided below.

The phrase "pharmaceutically acceptable carrier" is art recognized and includes a pharmaceutically acceptable material, composition or vehicle, suitable for administering compounds used in the methods described herein to subjects, e.g., mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Compounds of the Invention

Figure 3A:
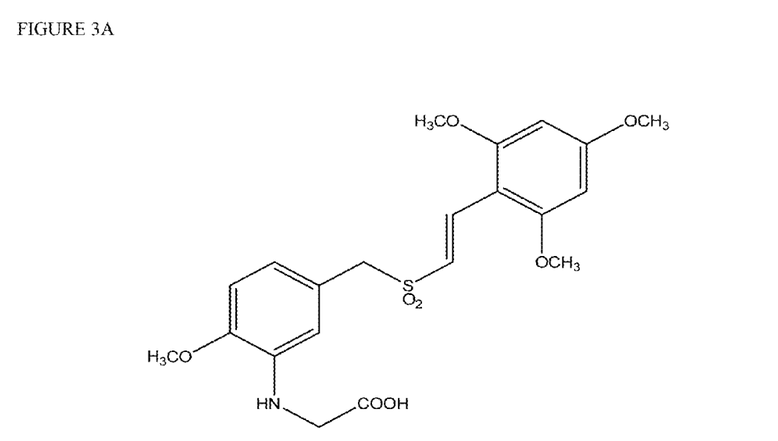
FIGS. 3A-3B shows the structures of (3A) ON01910 and (3B) nucleotide analog chemotherapeutic agents cladribine, clofarabine, fludarabine, mercaptopurine, pentostatin, thioguanine (tioguanine), capecitabine, cytarabine (Ara-C), decitabine, fluorouracil, floxuridine, sapacitabine and gemcitabine, as indicated.
Figure 3B:
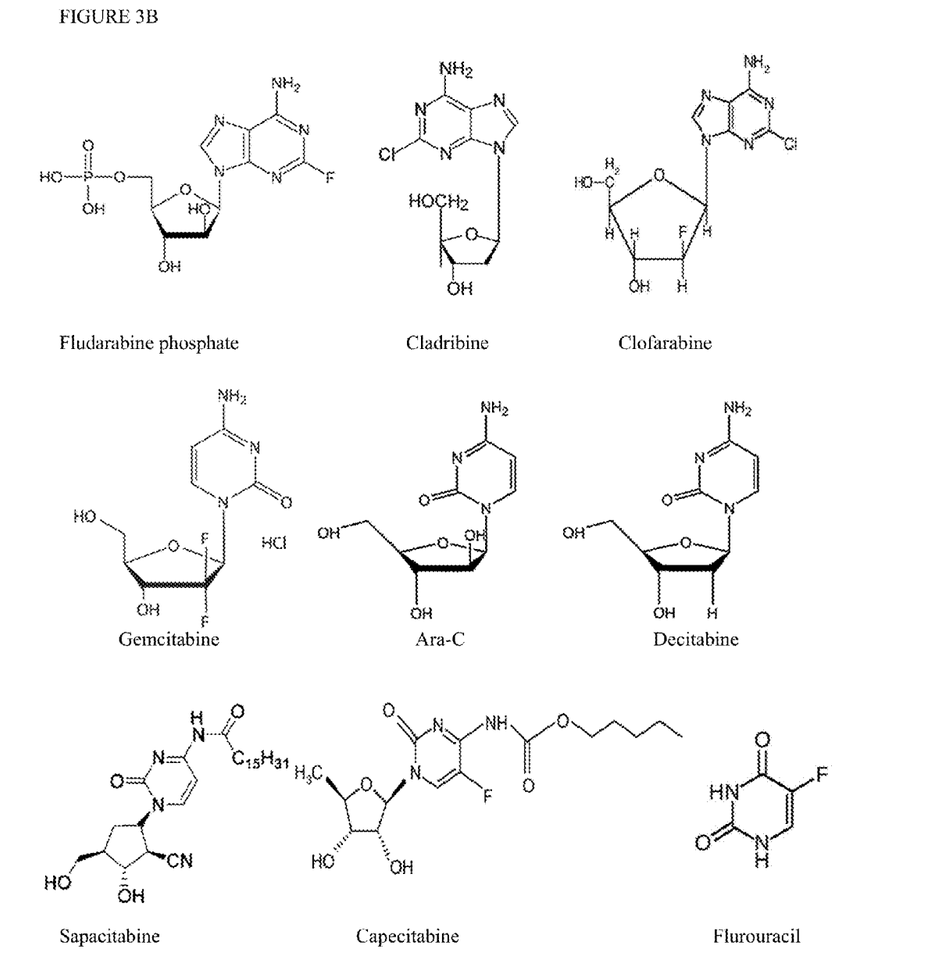

Preferred compositions and methods of the invention include the use of the Plk1 inhibitor ON-01910-Na ((E)-2,4,6-Trimethoxystyryl-3-(carboxymethylamino)-4-methoxybenzylsulfone (FIG. 3A) and gemcitabine (4-amino-1-[3,3-difluoro-4-hydroxy-5-(hydroxymethyl) tetrahydrofuran-2-yl]-1H-pyrimidin-2-one), also known as Gemzar® (FIG. 3B).

The term "mitotic disruptor/Plk pathway inhibitor" and the like as used herein include any composition which inhibits the kinase activity of a Plk (e.g., Plk1, Plk2, Plk3, or Plk4) or the activity of a Plk in a cell, for example by reducing expression of a Plk, or inhibits the activity of a Plk directly or by inhibiting a component of the Plk signaling pathway, particularly Plk1; and have activity as a mitotic disruptor. In a preferred embodiment, the inhibitor inhibits preferentially inhibits the activity of a Plk as compared to the activity of non-Plk kinases. The Plk inhibitor preferably has a 2-fold, 5-fold, 10-fold, or 20-fold greater activity in inhibiting Plk kinase activity as compared to inhibition of non-Plk kinases. A Plk inhibitor can be specific for one or more Plk isoforms. Alternatively, activity of a Plk inhibitor can be measured by comparing kinase activity of Plk in the presence and in the absence of an inhibitor. A Plk inhibitor inhibits Plk kinase activity at least 20%, at least 30%, at least 40%, at least 50%, at least 60%, at least 70%, at least 80%, or at least 90% relative to an untreated control.

Plk inhibitors can inhibit the activity of Plk in a cell by inhibiting the expression of Plk in a cell, for example using a Plk targeted antisense or siRNA agent targeted to a Plk of the appropriate species (e.g., human Plk1 is GenBank No NM_005030, version 3, updated Apr. 6, 2008; human Plk2 is Gen Bank No. NM_006622, version 2, updated Feb. 10, 2008; human Plk3 is GenBank No. NM_004073, version 2, updated Feb. 11, 2008; human Plk4 is GenBank No. Y13115, version 1, updated Oct. 17, 2006; all GenBank numbers incorporated herein by reference). Methods to design, synthesize, test, and administer antisense oligonucleotides and siRNA compounds are known in the art. For example, see US Patent Publications 20050107328 and 20070265438, both of which are incorporated herein by reference.

Activity of Plk1 in a defined quantity of cells or cell extract treated with a compound to reduce or inhibit expression of Plk is compared with the same defined quantity of untreated cells or cell extract Inhibition can be measured using any standard kinase assay such as those disclosed herein or, for example in PCT publication WO 03/072062, incorporated herein by reference. Mitotic disruptors and Plk inhibitors of the invention also disrupt mitosis as can be readily observed by microscopy, fluorescence activated cell sorting, or other methods.

Mitotic disruptors prevent the completion of proper mitosis for example, by disrupting centrosome distribution, failure of cytokinesis, abnormal chromosome numbers, and irreversible blocks at cell cycle checkpoints. Mitotic disruptors for use in the method of the invention prevent the completion of mitosis in at least about 5%, 10%, 20%, 30%, 40%, 50%, 60%, 70%, 80%, 90%, 95% or more of cells as compared to an untreated control.

In various embodiments of the invention, the mitotic disruptor/Plk pathway inhibitor is a small molecule. As used herein, the term "small molecule" refers to organic compounds, whether naturally-occurring or artificially created (e.g., via chemical synthesis) that have relatively low molecular weight (e.g., less than about 7500, less than about 5000, less than about 1000 molecular weight or less than about 500 molecular weight) and that are not proteins, polypeptides, or nucleic acids. Typically, small molecules have a molecular weight of less than about 1500 g/mol. Also, small molecules typically have multiple carbon-carbon bonds. In one embodiment, small molecules do not exclusively comprise peptide (amide) bonds. In another embodiment, small molecules are not oligomeric. Exemplary small molecule compounds include, but are not limited to, peptidomimetics, small organic molecules (e.g., Cane et al. 1998. *Science* 282:63; incorporated herein by reference), and natural product extract libraries. In another embodiment, the compounds are small, organic non-peptidic compounds. In a further embodiment, a small molecule is not biosynthetic. For example, a small molecule is preferably not itself the product of transcription or translation.

In various embodiments of the invention, the mitotic disruptor/Plk pathway inhibitor is a nucleic acid therapeutic. As used herein, the term "nucleic acid therapeutic agent" and the like refers to any nucleic acid-based compound that contains nucleotides and has a desired effect on a target gene. The nucleic acid therapeutic agents can be single-, double-, or multiple-stranded, and can comprise modified or unmodified nucleotides or non-nucleotides or various mixtures, and combinations thereof. Examples of nucleic acid therapeutic agents of the disclosure include, but are not limited to, antisense nucleic acids, dsRNA, siRNA, and enzymatic nucleic acid compounds.

Plk1 inhibitors can include any of a number of derivatives of ON-01910-Na which inhibit the activity of Plk1, preferably that specifically inhibit the activity of Plk1. For example, Plk1 inhibitors includes "ON01910-Na and derivatives thereof" which are understood as any compound of the formula (I):

wherein:

X is selected from the group consisting of (i) and (ii) below:

$X^1$ is selected from the group consisting of (i), (ii) and (iii) below:

wherein $X^1$ is optionally protected with one or more chemical protecting groups;

g is 0 or;

each M is a bivalent connecting group independently selected from the group consisting of —($C_1$-$C_6$)alkylene-, —($CH_2$)$_a$—V—($CH_2$)$_b$—, —($CH_2$)$_d$—W—($CH_2$)$_e$— and —Z—;

each y is independently selected from the group consisting of 0 and 1;

each V is independently selected from the group consisting of arylene, heteroarylene, —C(=O)—, —C(=S)—, —S(=O)—, —$SO_2$—, —C(=O)O—; —C(=O)($C_1$-$C_6$) perfluoroalkylene-, —C(=O)$NR^4$—, —C(=S)$NR^4$— and —$SO_2NR^4$—;

each W is independently selected from the group consisting of —$NR_4$—, -0- and —S—;

each a is independently selected from the group consisting of 0, 1, 2 and 3;

each b is independently selected from the group consisting of 0, 1, 2 and 3;

each d is independently selected from the group consisting of 1, 2 and 3;

each e is independently selected from the group consisting of 0, 1, 2 and 3;

wherein the absolute stereochemistry of —Z— is D or L or a mixture of D and L;

each $R^a$ is independently selected from the group consisting of —H, —($C_1$-$C_6$)alkyl, —($CH_2$)$_3$—NH—C($NH_2$)(=NH), —$CH_2$C(=O)$NH_2$, —$CH_2$COOH, —$CH_2$SH, —($CH_2$)$_2$C(=O)—$NH_2$, ($CH_2$)$_2$COOH, CH2-(2-imidazolyl), —CH($CH_3$)—$CH_2$—$CH_3$, —$CH_2$CH($CH_3$)$_2$, —($CH_2$)$_4$—$NH_2$, —($CH_2$)$_2$—S—$CH_3$, phenyl, $CH_2$-phenyl, —$CH_2$—OH, —CH(OH)—$CH_3$, —$CH_2$-(3-indolyl), —$CH_2$-(4-hydroxyphenyl), —CH($CH_3$)$_2$ and —$CH_2$—$CH_3$; and includes compounds wherein $R^a$ and $R^1$ combine to form a 5-, 6- or 7-membered heterocyclic ring;

each $R^1$ is independently selected from the group consisting of —H, unsubstituted aryl, substituted aryl, substituted heterocyclic, unsubstituted heterocyclic, —$CO_2R^5$, —C(=O)$NR^4_2$, —$CR^4R^6R^7$, —C(=NH)—$NR^4_2$, —($C_1$-$C_6$)perfluoroalkyl, —$CF_2Cl$, —P(=O)(O$R^4$)$_2$, —OP(=O)(O$R^4$)$_2$ and a monovalent peptidyl moiety with a molecular weight of less than 1000; provided that when y is 0 and R' is —$CO_2R^5$, $R^5$ is not —H;

each $R^2$ is independently selected from the group consisting of —H, —($C_1$-$C_6$)alkyl, and aryl($C_1$-$C_3$)alkyl, wherein —$R^2$ and -(M)$_y$-$R^1$ may optionally be linked covalently to form a 5-, 6- or 7-membered substituted or unsubstituted heterocycle;

each $R^3$ is independently selected from —($C_1$-$C_6$)alkyl;

each $R^4$ is independently selected from the group consisting of —H, and —($C_1$-$C_6$)alkyl;

each $R^5$ is independently selected from the group consisting of —H, —($C_1$-$C_6$)alkyl and —($C_1$-$C_6$)acyl;

each $R^6$ is independently selected from the group consisting of —H, —($C_1$-$C_6$)alkyl, —$CO_2R^5$, —C(=O)$R^7$, —O$R^5$, —OC(=O)($CH_2$)$_2$$CO2R^5$, —$SR^4$, guanidine, —$NR^4_2$, —$NR^4_3{}^+$, —$N^+$($CH_2CH_2OR^5$)$_3$, phenyl, substituted phenyl, heterocyclic, substituted heterocyclic and halogen;

each $R^7$ is independently selected from the group consisting of —$R^a$, halogen, —$NR^4_2$, and heterocycles containing two nitrogen atoms; and Q is selected from the group consisting of —H, —($C_1$-$C_6$)alkoxy, halogen, —($C_1$-$C_6$)alkyl and $^-NR^4_2$;

wherein the substituents for the substituted aryl and substituted heterocyclic groups comprising or included within $R^1$, $R^2$, $R^a$, $R^6$ and $R^7$, are independently selected from the group consisting of halogen, ($C_1$-$C_6$)alkyl, —$NO_2$, —C≡N, —$CO_2R^5$, —C(=O)O($C_1$-$C_3$)alkyl, —$OR^5$, —($C_2$-$C_6$)alkylene-OH, phosphonato, —$NR^4_2$, —NHC(=O)($C_1$-$C_6$)alkyl, sulfamyl, —OC(=O)($C_1$-$C_3$)alkyl, —O($C_2$-$C_6$)alkylene-N(($C_1$-$C_6$)alkyl)$_2$ and —$CF_3$;

provided:
(1) when $R^1$ is a monovalent peptidyl moiety of molecular weight less than 1000 and V is —C(=O)—, —C(=S)—, —S(=O)— or —$SO_2$—, and b is 0;
then said peptidyl moiety is coupled to M through the amino terminus of the peptidyl moiety or through a sidechain amino group to form an amide, thioamide, sulfinamide or sulfonamide respectively;

(2) when $R^1$ is a monovalent peptidyl moiety of molecular weight less than 1000 and V is —C(=O)$NR^4$ or $SO_2NR^4$ and b is 0,
then said peptidyl moiety is coupled to M through the carboxy terminus of the peptidyl moiety or through a sidechain carboxyl group to form an imide or sulfonamide, respectively; and (3) when $R^1$ is a monovalent peptidyl moiety of molecular weight less than 1000 and W is —$NR^4$—, —S— or —O—, and a is 0,
then said peptidyl moiety is coupled to M through the carboxy terminus of the peptidyl moiety or through a sidechain carboxyl group to form a carboxamide, carbothioic acid ester or the carboxylic ester respectively; or a salt of such a compound.

Other ON01910-Na derivatives, methods of synthesis, and activity of compounds can be found in PCT publication WO 03/072062.

As used herein, a "nucleotide analog chemotherapeutic agent" is a purine analog such as cladribine, clofarabine, fludarabine, mercaptopurine, pentostatin, and thioguanine; or a pyrimidine analog such as capecitabine, cytarabine, decitabine, fluorouracil, floxuridine, sapacitabine, and gemcitabine. Such compounds are structurally similar, as shown in FIG. 3, and typically have a nitrogen attached to the sugar group and act at least by disrupting DNA synthesis. Such compounds are known in the art.

Dosage and Formulation

The compounds of the invention can be administered topically, enterally, or parenterally. Topical administration, for example, includes but is not limited to epicutaneous, enema, eye drops, ear drops, intranasal, and vaginal administration. Enteral administration, for example, by mouth (orally), by gastric feeding tube, duodenal feeding tube, or gastrostomy, and rectally, in suppository or enema form. Parenteral administration includes, but is not limited to, intravenous, intraarterial, intramuscular, intracardiac, subcutaneous, intraosseous infusion (into the bone marrow), intradermal, intrathecal, and intraperitoneal.

In a preferred embodiment, the compounds of the invention are administered intravenously.

The compounds used in the methods of the present invention can be administered orally using any pharmaceutically acceptable dosage form known in the art for such administration. The compound can be supplied in solid dosage forms such as dry powders, granules, tablets or capsules, or in liquid dosage forms, such as syrups or aqueous suspensions. The compound can be administered alone, but is generally administered with a pharmaceutical carrier. A valuable treatise with respect to dosage forms is Remington's Pharmaceutical Sciences, Mack Publishing.

The compounds used in the methods of the present invention can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the art.

The compounds used in the methods of the invention can be administered by any means that produces contact of the compound with the compound's site of action in the body of a host, such as a human or a mammal They can be administered alone or with a pharmaceutical carrier selected on the basis of the chosen route of administration and standard pharmaceutical practice.

The dosage regimen for the compounds determined from the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. An ordinarily skilled physician or veterinarian can readily determine an effective amount of the compound to administer to a subject.

The compounds used in the methods of the present invention can be administered in intranasal form via topical use of suitable intranasal vehicles, or via transdermal routes, using those forms of transdermal skin patches wall known to those of ordinary skill in that art.

In the methods of the present invention, the compounds described herein can be administered in admixture with suitable pharmaceutical diluents, excipients, or carriers (collectively referred to herein as carrier materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or .beta.-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds used in the methods of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds used in the methods of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds determined from the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates, and crosslinked or amphipathic block copolymers of hydrogels.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions.

Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol. Compounds administered intravenously are frequently delivered in normal saline.

Suitable pharmaceutical carriers are described in Remington's Pharmaceutical Sciences, Mack Publishing Company, a standard reference text in this field. Formulation in the appropriate carrier is within the ability of those skilled in the art.

Nucleotide Analog Chemotherapeutic Agent Dosing

Dosing regimens of nucleotide analog chemotherapeutic agents are known in the art and vary depending on the severity and type of cancer to be treated. Some examples of chemotherapeutic regimens are provided in the table below. All listed references are incorporated herein by reference.

| Chemotherapeutic agent | Disease Regimen | Reference |
|---|---|---|
| cladribine | Indolent non-Hodgkin lymphoma 0.14 mg/kg/day x 5 days every 4 weeks x 6 | Blum et al, *Cancer* 107: 2817-2825. 2006 |
| | Indolent lymphoproliferative disorders and mantle cell lymphoma 1. rituxamab 375 mg/m$^2$ day 1, cladribine 0.12 mg/kg/day, days 2-6 every 4 weeks 2. rituxamab 375 mg/m$^2$ day 1, cladribine 0.12 mg/kg/day, days 2-4, and cyclophosphamide 250 mg/m$^2$ days 2-4 every 4 weeks | Robak et al., *Cancer* 107: 1542-1550, 2006. |
| clofarabine | Chronic lymphocytic leukemia 3-4 mg/m$^2$/day, days 1-5 every 4 weeks 15 mg/m$^2$/day, days 1-5 every 4 weeks | Ghandi et al., *Cancer Therapy* 12: 4011-4017 |
| fludarabine | Chronic lymphocytic leukemia 25 mg/m$^2$/day, days 1-5 every 4 weeks 25 mg/m$^2$/day, days 1-5 every 4 weeks + 20 mg/m$^2$ chlorambucil every 4 weeks | Rai et al., *NEJM* 343: 1750-1757, 2000. |
| mercaptopurine | Acute lymphoblastic leukemia Oral - 75 mg/m$^2$/day, days 0-70* IV- 1000 mg/m$^2$/day, days 0, 7, 14, 21, 28, 35, 42, 49, 56, 63, and 70* | Bostrom et al., *Blood* 101: 3809-3817, 2003. |
| pentostatin | Chronic lymphocytic leukemia 2 mg/m$^2$ pentostatin, 600 mg/m$^2$ cyclophosphamide, 375 mg/m$^2$ rituximab every 21 days, 6 cycles | Kay et al. *Blood*. 109: 405-411, 2007. |
| thioguanine | Malignant glioma 30 mg/m$^2$ oral 6 thioguanine every 6 hours for 12 doses (hours 0-66); 50 mg/m$^2$ oral procarbazine every 6 hours, 4 doses (hours 60-78); 400 mg/m$^2$ oral dibromodulcitol, 1 dose (hour 60); 110 mg/m$^2$ oral lomustine, 1 dose (hour 72); 1.4 mg/m$^2$ i.v. vincristine days 14 and 28 every 6-7 weeks x 6. | Levin et al., *Neuro-oncology*, 2: 22-28. |
| capecitabine | Rectal cancer 100 mg/m$^2$ oral capecitabine twice daily, days 1-14 and 25-38 + escalating doses of oxaliplatin. | Hospers et al., *Ann. Surg. Oncol*. 14: 2773-2779, |
| cytarabine | Myeloid leukemia 100 mg/m$^2$ cytarabine continuous infusion days 1-5 and 5 mg/m$^2$ idarubicin continuous infusion days 1-5. | von Lilienfeld-Toal et al., *Hemtolog* 92: 1719-1720 |

-continued

| Chemotherapeutic agent | Disease Regimen | Reference |
|---|---|---|
| decitabine | Melanoma or renal cell cardinoma 0.1-0.3 mg/kg/dose subcutaneous, days 1-5 and 8-12, with high dose IL-2 weeks 3-4 and 6-8, optional 2 additional cycles every 12 weeks | Gollob et al., *Clin. Can. Res.* 12: 4619-4627. |
| fluorouracil | Gastric cancer 150 mg/m2 irinotecan day 1 and 20 mg/m$^2$ IdLV followed by 400 mg/m$^2$ (bolus) and 600 mg/m$^2$ (22 hours continuous infusion) 5-FU days 1 and 2 every 14 days | Kim et al., *Jpn. J. Clin. Oncol.* 37: 744-749. |
| floxuridine | Metastatic colon cancer Gastroduodenal artery infusion 500 mg FUDR, 50 mg oxaliplatin, 2.5 mg dexamethasone. | Xu et al., *Ann. Surg.* 245: 583-590. |
| sapacitabine | Solid tumors including prostate, breast, and lung 1.5, 12, 20, 25, 30, 50, 67, 90, 120, 160 and 220 oral mg/m$^2$/day, maximum tolerated dose 160 mg/m$^2$/day | Delaunoit et al., *Invest New Drugs*, 24: 327-333, 2006. |

*mercaptopurine was co-administered with vincristine, methotrexate, and prednisone or dexamethazone.

Gemcitabine Dosing

A number of gemcitabine dosing regimens have been established for the treatment of various cancers using gemcitabine alone, or in combination with other agents. For example, doses range from 10 mg/m$^2$/week to 1200 mg/m$^2$/week as a single agent or in combination with other chemotherapeutic agents were used in studies for the treatment of biliary tract cancer. The frequency and number of doses per cycle varied (see, e.g., Pastorelli et al., *Ann. Oncol.* 17:v153-157, 2006, incorporated herein by reference). Dosage ranges of 800 mg/m$^2$/week to 1000 mg/m$^2$/week were administered in studies for the treatment of stage IIIB or IV non-small cell lung cancer (see, e.g., Rocha Lima et al., *Ann. Oncol.* 15:410-418, 2004 incorporated herein by reference). Similar dosages were administered in studies for treatment of advanced transitional cell carcinoma of the urothelium, relapsed Hodgkin's lymphoma, pancreatic cancer, and renal cancer.

Examples of published dosing regimens are shown in the tables below.

Single agent administration in advanced bilary tract cancer, reproduced in part from Pastorelli et al, 2006.

| Authors | Gemcitabine dose schedule |
|---|---|
| Metzger et al. | 1000 mg/m$^2$/wk x 7 then 1 x/wk x 3 every 4 weeks |
| Valencak et al. | 1200 mg/m$^2$ days 1, 8, and 15 every 4 weeks. |
| Dobrilla -Dintinjana et al. | 1000 mg/m$^2$/wk x 7 |
| Kubika et al. | 10 mg/m$^2$/wk x 7 the 1/wk x 3 every 4 weeks |
| Arroyo et al. | 1000 mg/m$^2$ days 1, 8, and 15 every 4 weeks |
| Gebbia et al. | 1000 mg/m$^2$ days 1, 8, and 15 every 4 weeks |
| Penz et al. | 2200 mg/m$^2$ day 1 every 2 weeks |

Combination therapy with Doxetaxel (Dox) with gemcitabine (gem) in non-small cell lung cancer, reproduced in part from Rocha Lima et al., 2004.

| Study | Regimen |
|---|---|
| | Dox day 8- gem days 1 and 8 |
| Rebattu et al | Dox 85 mg/m$^2$ day 8 + gem 1000 mg/m$^2$ days 1 and 8, every 3 weeks |
| Amenedo et al | Dox 85 mg/m$^2$ day 8 + gem 1000 mg/m$^2$ days 1 and 8, every 3 weeks |
| Lizon et al. | Dox 75 mg/m$^2$ day 8 + gem 1000 mg/m$^2$ days 1 and 8, every 3 weeks |
| Georgoulias et al. | Dox 100 mg/m$^2$ day 8 + gem 900 mg/m$^2$ days 1 and 8 + G-CSF 150 µg/m$^2$ days 9-15, every 3 weeks |
| | Dox day 1- gem days 1 and 10 or 15 |
| Hejma et al. | Dox 80 mg/m$^2$ day 1 + gem 1000 mg/m$^2$ days 1 and 10 + G-CSF 5 µg/kg days 2-8, every 3 weeks |
| Vewntriglia et al. | Dox 75 mg/m$^2$ day 1 + gem 1000 mg/m$^2$ days 1 and 15, every 3 weeks |
| | Weekly and bi-weekly regimens |
| Popa et al. | Dox 40 mg/m$^2$ days 1 and 8 + gem 1000 mg/m$^2$ days 1 and 8, every 3 weeks |
| Menendez et la | Dox 36 mg/m$^2$ days 1, 8, and 15 + gem 1000 mg/m$^2$ days 1, 8, and 15, every 4 weeks |
| McKay et al. | Dox 30 mg/m$^2$ days 1, 8, and 15 + gem 800 mg/m$^2$ days 1, 8, and 15, every 4 weeks |
| Syrigos et al. | Dox 80 mg/m$^2$ day 1 + gem 1000 mg/m$^2$ day 1, every 15 days |
| Neubauer et al | Dox 36 mg/m$^2$ days 1, 8, 15, 22, 29, and 36 + gem 900 mg/m$^2$ days 1, 8, 22, and 29, every 8 weeks |

In the methods of the invention, gemcitabine can be administered at a dose of about 500 mg/m$^2$/week to about 1500 mg/m$^2$/week, preferably about 700 mg/m$^2$/week to about 1300 mg/m$^2$/week, preferably about 800 mg/m$^2$/week to about 1200 mg/m$^2$/week. Higher and lower dosage rates are possible. The dose may be administered in a single dose per week or may be divided into multiple doses. The rate of the dosing (time over which the dose is administered) can be varied. The frequency of the dosing can be 1, 2, 3, or more times per cycle. The cycle can be 1, 2, 3, 4, 5, 6, 7, 8 or more weeks. The number of cycles can be 1, 2, 3, 4, 5, 6, 7, 8, 9, 10 or more cycles, or until the desired therapeutic outcome is achieved, or until dosing is limited by side effects.

ON01910 Dosing

ON01910-Na has been explored in clinical trials using different dosages and administration schedules. In one study, dosage ranges have been 160-8740 mg/week, with the dose divided into two doses per week administered on three consecutive weeks every four weeks. (2-hour infusion 2/week for 3 consecutive weeks every 4 weeks. The dose range explored was 80 mg-4370 mg. The dose per this schedule being recommended for further testing is 3120 mg.) Assuming a body surface area of about 1.8 m$^2$, the dose is about 90 mg/m$^2$/week to about 4850 mg/m$^2$/week.

In another study, ON01910-Na was administered as a 24-hour infusion on a weekly continuous schedule. The dose range was 250 mg/m$^2$/week-2750 mg/m$^2$/week.

In another study, ON01910-Na was administered as a 72-hour infusion every 2 weeks. The dose range was 50 mg/m$^2$/day-400 mg/m$^2$/day (i.e., 75 mg/m$^2$/week to 600 mg/m$^2$/week).

The safety profile of ON01910-Na was determined in two standard toxicology animal studies using rats and dogs. In rats, single doses of 300 and 600 mg/m$^2$ produced no toxicity, and 1200 mg/m$^2$ had only slight toxicity (anogenital staining). When the dose was increased to 3000 mg/m$^2$, 9 of 11 animals died. In 7 day repeat dosing (1200 mg/m$^2$), 2 of 13 rats died during the dosing period. In 28 day repeat dosing, using groups of 12 male rats and 12 female rats, fixed daily doses of 180 mg/m$^2$ and 450 mg/m$^2$ were tolerated. A dose of 900 mg/m$^2$ given twice per week for 4 weeks was well tolerated. In dogs, acute single doses of 2000 and 4000 mg/m$^2$ produced gastrointestinal effects (diarrhea, flatulence), with other signs of discomfort during dosing (struggling, vocalization). In 7 day repeat intravenous dosing, 1000 mg/m$^2$ daily was well tolerated by dogs. In 28 day repeat dosing, daily intravenous doses of 200 and 500 mg/m$^2$ were well tolerated for 28 days in groups consisting of three male and three female beagle dogs. A high dose group started at 1000 mg/m$^2$ showed no signs of toxicity after 8 days. Based on dose escalation studies, a highest non-severe toxic dose for this dose schedule was estimated to be about 1500 to 2000 mg/m$^2$ for 28 days. A separate group of 6 dogs treated at 1000 mg/m2 twice per week for 4 weeks tolerated the compound well without clinical problems. There was no evidence of significant myelotoxicity, neuropathy, or cardiotoxicity in these toxicology studies. Results are summarized in the table below. (reproduced from Gumlreddy et al., *Cancer Cell*, 7:275-286, 2005. Incorporated herein by reference.)

| Species | Dose schedule IV bolus | MTD mg/m$^2$ | STD/LD$_{10}$ mg/m$^2$ | HNSTD mg/m$^2$ |
| --- | --- | --- | --- | --- |
| Rats | Single dose | >1200 (no deaths) | <3000 (9/11 died) | — |
| Rats | 7 day repeat | | 1200 (2/13 died) | — |
| Rats | 2 x/wk, 4 wks | | <2100 (5/9 died) | — |
| Rats | 28 day repeat | 450 (1/36 died) | <900 n(11/36 died) | — |
| Rats | 2x/wk, 4 wk | 900 (1/24 died) | | — |
| Dogs | Single dose | >4000 | | 2000 |
| Dogs | 7 day repeat | >1000 | | >1000 |
| Dogs | 2x/wk, 4 wks | >1000 | | |
| Dogs | 28 day repeat | >1000 | 2500 | 1500-2000 |

MTD, maximum tolerated dose; STD, severely toxic dose; LD10, dose producing lethality in 10% of animals; HNSTD, highest non-severely toxic dose.

In the methods of the invention, ON01910-Na and derivatives thereof can be administered at a dose of about 50 mg/m$^2$/week to about 5000 mg/m$^2$/week, or about 90 mg/m$^2$/week to about 4850 mg/m$^2$/week. Higher and lower dosage rates are possible. The dose may be administered in a single dose per week or may be divided into multiple doses. The rate of the dosing (time over which the dose is administered) can be varied. The frequency of the dosing can be 1, 2, 3, or more times per cycle. The cycle can be 1, 2, 3, 4, 5, 6, 7, 8 or more weeks. The number of cycles can be 1, 2, 3, 4, 5, 6, 7, 8, 9, 10 or more cycles, or until the desired therapeutic outcome is achieved, or until dosing is limited by side effects.

As shown above in the table from Rocha Lima, schedules and dosing for administration of gemcitabine as a single agent or in a combined chemotherapeutic regimen are similar. Any of the regimens provided in the table above or in the art for dosing of gemcitabine can be combined with the dosing regimens set forth above for ON01910-Na or derivatives thereof. It is understood that a physician or other practitioner skilled in oncology can vary dosing regimens for appropriate individuals and that other dosing regimens are possible.

It is understood that specific dosages and timing of administration is modified with chemotherapeutic agents in accordance with undesirable side effects (e.g., neutropenea, infection, nausea) which commonly occur with administration of chemotherapeutic agents.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Unless specifically stated or obvious from context, as used herein, the term "or" is understood to be inclusive.

Unless specifically stated or obvious from context, as used herein, the terms "a", "an", and "the" are understood to be singular or plural.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

All references, patents, patent applications, and Accession Numbers as of the filing date of the priority application referred to herein are specifically incorporated by reference.

This invention is further illustrated by the following examples, which should not be construed as limiting.

EXAMPLES

Materials and Methods

In Vitro Proliferation Assay

Gemcitabine resistant pancreatic human tumor cell lines 813, 1005, MP2, (commercially available from ATCC) and E3JD13, XPa3, and XPa4 (obtained from low passages of tumors at JHU) were grown under standard culture conditions in RPMI-1640 with 10% febal bovine serum and 1% penicillin/streptomycin.

Plk1 siRNA and transfection reagent (Dharmacon RNA technologies, Lafayette, Colo.) were optimized in 24-well cell culture plates where 30,000 cells were added to each well in 500 µL growth media and grown overnight at 37° C. Each plate contained wells for antiobiotic-free media alone, wells for 0.2%, 0.4% and 0.6% of transfection reagent (TR) to final volume with antibiotic-free media to check toxicity and wells for the varying TR amount plus 100 nM and 200 nM siRNA concentrations in antibiotic-free media. Conditions were tested for 24 and 48 hours. Cells were harvested with RLT buffer (Qiagen Valencia, Calif.). After optimization of siRNA conditions for Plk1 inhibition in all six cell lines, the optimal concentration of TR, siRNA and time were 0.4%, 200 nM and 48 hours, respectively.

Total RNA was extracted from cell pellets (and tumors) using the RNeasy™ Mini Kit (Qiagen, Valencia, Calif.). cDNA was synthesized using iScript cDNA synthesis kit (Bio-Rad, Hercules, Calif.) following the manufacturer's instructions. Relative quantification of Plk1 and ubiquitin C (UBC, used as housekeeper gene) mRNA was achieved using an iCycler iQ real-time PCR detection system (Bio-Rad) using ABI Taqman probes (Foster City, Calif.). The experiments were repeated twice and samples were run in quadruplicate.

In vitro drug sensitivity to gemcitabine, ON 01910.Na and the combination of both (all at concentrations of 1 μM for 72 hours) was assessed by 3-(4,5-dimethylthiazol-2-yl)-2,5-diphenyltetrazolium bromide (MTT; Sigma, St Louis, Mo.). For the MTT-based efficacy studies after siRNA, cells were seeded in 96-well plates, transfected during 48 hours with the above conditions, and then exposed to either vehicle or gemcitabine at a concentration of 1 μM for 72 hours. Each experiment was performed in sextuplicate for each drug concentration and was carried out independently at least 3 times.

Direct Pancreatic Cancer Derived Xenograft

Resected pancreatic adenocarcinomas are routinely implanted in nude mice at the Johns Hopkins Medical Institutions as a method to obtain enriched populations of neoplastic cells under an IRB-approved protocol from residual pancreatic cancer tumors. Briefly, tumor specimens from Whipple resection specimens were divided into 2-3 mm$^3$ pieces in antibiotic-containing RPMI media. Pieces of non-necrotic tissue were selected and immersed in Matrigel. Under anesthesia with isofluorane, tumors were implanted into five-to-six week-old female athymic (nu/nu) mice purchased from Harlan (Harlan Laboratories, Washington, D.C.).

Tumor bearing mice were divided into four groups (n=8-10 tumors per group). Mice were treated with Gemcitabine 100 mg/kg, 2 times/week for 4 weeks, or with ON-01910.Na 250 mg/kg/day for 4 weeks, or a combination thereof. Tumor size was determined using calipers every four days for the course of the experiment.

On day 28, animals were euthanized and tumors were removed for Plk1 expression analysis by RT-PCR using standard protocols. Plk1 expression levels were expressed relative to expression in non-drug treated control.

Drugs

Gemcitabine (Eli Lilly, Indianapolis, Ind.) was dissolved in saline. The drug was freshly prepared and used at an injection volume of 0.2 mL/20 g body weight.

ON-01910-Na was dissolved in saline. The drug was freshly prepared and used at an injection volume of 0.2 mL/20 g body weight.

Relative Tumor Growth Inhibition

Relative tumor growth inhibition (TGI) was calculated as TGI=(Ti−T0/Ci−C0), where Ti and Ci represent tumor size in the treated and control group at 28-day, respectively; T0 and C0 represent tumor size in the treated and control group at 1-day, respectively. Experiments were terminated on day 28. We defined a xenograft as sensitive and resistant to gemcitabine if TGI≤−30% and TGI>−30%, respectively, according to the RECIST criteria.

Example 1

Inhibition of Plk1 Overcomes Gemcitabine Resistance in Pancreatic Tumor Cell Lines Six gemcitabine resistant cell lines were grown in culture and treated with gemcitabine alone, an siRNA targeted to Plk1, or a combination thereof for 24 hours. Cells were grown for an additional three days in media. Percent cell growth relative to a control was determined.

Similarly, the same cell lines were grown in the presence of gemcitabine alone, Plk1 alone, or a combination thereof for three days. Percent cell growth relative to a control was determined.

Figure 1A:
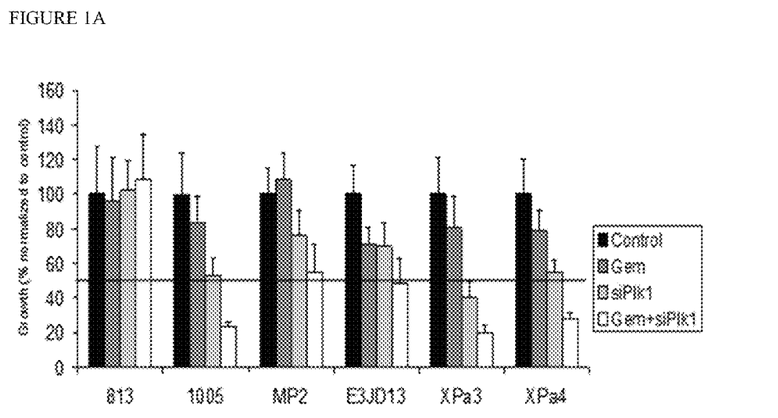
FIGS. 1A and B are graphs showing inhibition of growth of six gemcitabine resistant cell lines in response to treatment with gemcitabine in the presence or absence of (1A) an siRNA Plk1 inhibitor and (1B) ON-01910-Na, a small molecule Plk1 inhibitor.
Figure 1B:
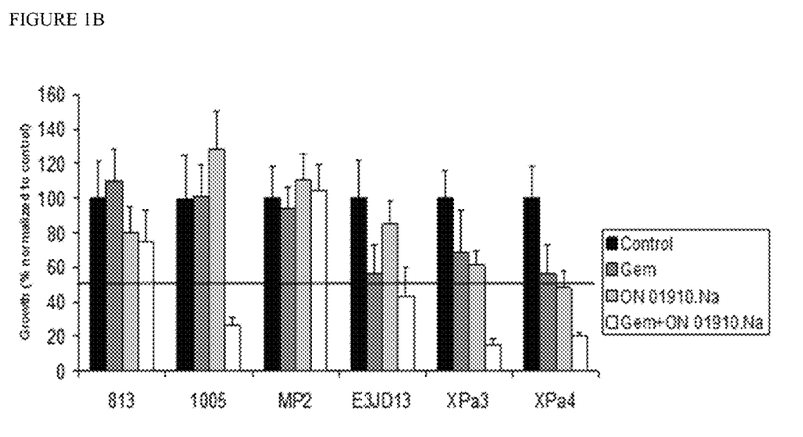

Growth was inhibited by the Plk1 siRNA in three out of the six cell lines (FIG. 1A) and ON-01910-Na (FIG. 1B) in two out of the six cell lines, relative to an untreated control. Treatment with a Plk1 inhibitor in combination with gemcitabine strongly inhibited growth in most cell lines. The combination of ON-01910-Na and gemcitabine had at least a significantly additive or synergistic effect in inhibiting cell growth in three cell lines, 1005, XPa3, and XPa4. These data demonstrate that a Plk1 inhibitor can be an effective at killing gemcitabine resistant cells, and that Plk1 inhibitors can sensitize gemcitabine resistant cells to killing by gemcitabine.

Example 2

Inhibition of Plk1 Overcomes Gemcitabine Resistance in Pancreatic Tumors In Vivo Pancreatic tumors were implanted in mice as detailed above. Mice were treated with gemcitabine alone, ON-01910-Na alone, or a combination thereof as indicated. Tumor size was measured at four day intervals.

Figure 2A:
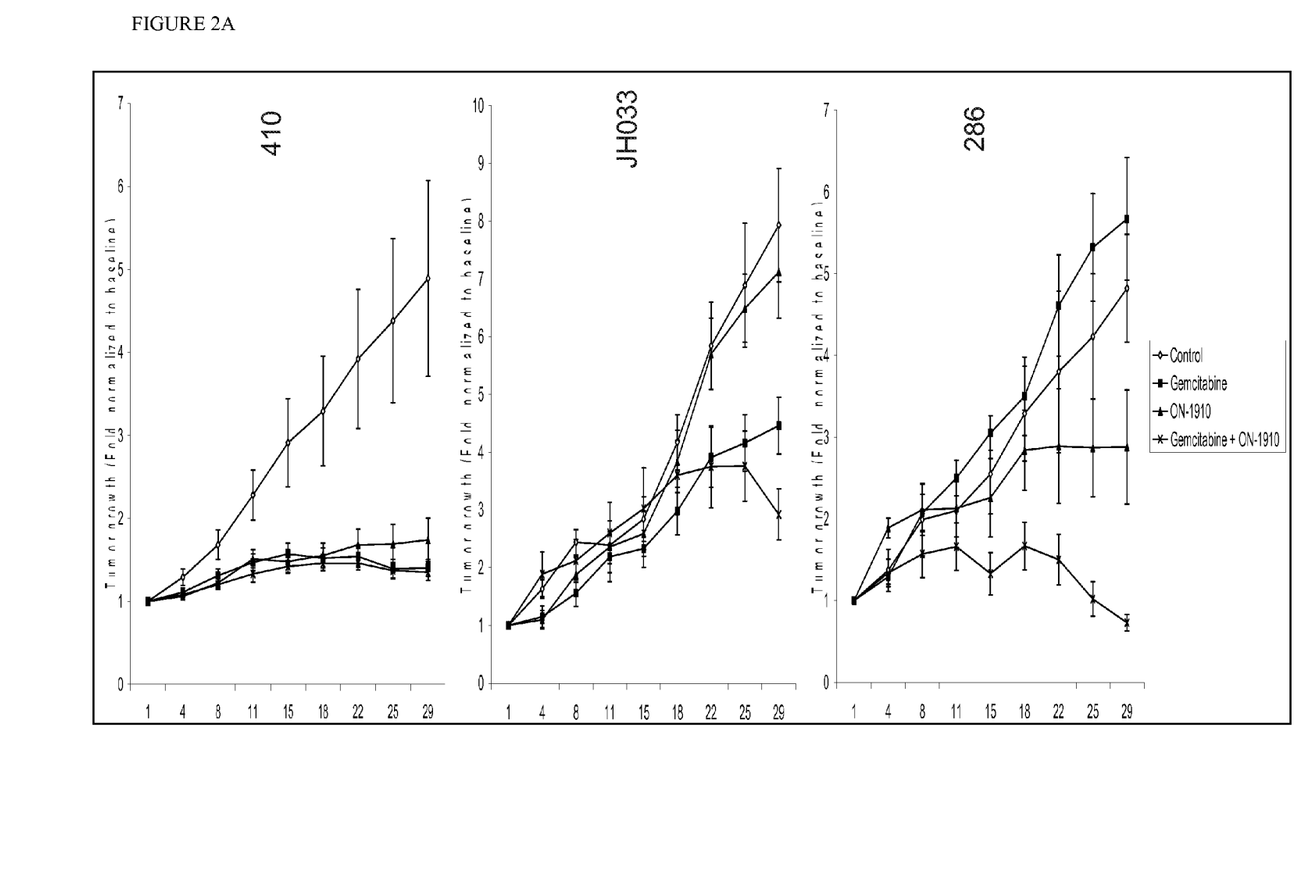
Figure 2B:
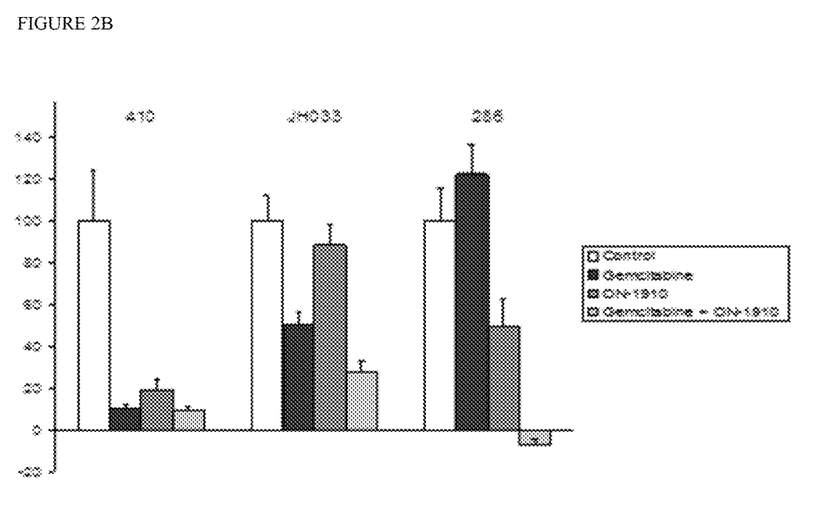

The three pancreatic tumors demonstrated different susceptibility profiles to each gemcitabine and ON-01910-Na (FIG. 2A). Tumor 41 was susceptible to treatment with both gemcitabine and ON-01910-Na with essentially no tumor growth regardless of treatment. Tumor JH03 was susceptible to treatment with gemcitabine alone, but not ON-01910-Na. However, the combination of gemcitabine and ON-01910-Na was more effective than gemcitabine alone by the end of the experiment on day 28. Tumor 28 was gemcitabine resistant and ON-01910-Na sensitive. Notably, the combination of gemcitabine and ON-01910-Na was significantly more effective than either of the compounds alone.

On day 28, tumors were harvested and analyzed for Plk1 expression (FIG. 2C). As shown, the JH03 tumor which had the lowest expression of Plk1 after exposure to gemcitabine was most susceptible to treatment with gemcitabine.

These data demonstrate that ON-01910-Na can induce gemcitabine sensitization in gemcitabine resistant pancreatic tumors.

Example 3

Treatment of a Subject Having a Cancer Susceptible to Treatment with a Nucleotide Analog Chemotherapeutic Agent A subject is diagnosed with advanced bilary tract cancer which is susceptible to treatment with gemcitabine. Surgery is performed to reduce tumor burden. Chemotherapy is initiated to reduce and treat metastatic cancer and any remaining cancer at the primary site. Gemcitabine is administered to the subject at 1000 mg/m² on days 1, 8, and 15 every 4 weeks for two cycles. Beginning at the third cycle, ON01910 is co-administered as a 24-hour infusion on a weekly continuous schedule (days 1, 8, 15, and 23 of the four week cycle). The dose of ON01910 is 1000 mg/m²/week. The drugs are co-administered for the remaining cycles of the chemotherapy regimen. The subject is monitored for disease progression or regression.

Example 4

Prevention of the Development of Gemcitabine Resistance by Co-Administration of an siRNA Targeted to Plk1

A subject is diagnosed with pancreatic cancer. An siRNA compound targeted to Plk1 is administered to the subject concurrent with the first dose of gemcitabine chemotherapy during each cycle (i.e., on day 1 of each four week cycle). SiRNA therapeutics are long acting compounds allowing for relatively infrequent administration relative to administration of gemcitabine. Gemcitabine chemotherapy is continued for the desired number of cycles. The subject is monitored for disease progression or regression.

Example 5

Prevention of the Development of Resistance to a Nucleotide Analog Chemotherapeutic Agent Resistance Using ON01910

A subject is diagnosed with chronic lymphocytic leukemia, a cancer susceptible to treatment with fludarabine administered intravenously at a dose of 25 mg/m² daily for 5 days every 28 days for up to 12 cycles. One week prior to the first administration of fludarabine to the subject, ON01910 is administered at a dose of 100 mg/m²/day in a 72 hour infusion (300 mg/m² total dose). Administration of ON01910 at the same dose every other week is continued throughout the course of fludarabine chemotherapy. The subject is monitored for disease progression or regression.

INCORPORATION BY REFERENCE

The contents of all references, patents, pending patent applications and published patents, cited throughout this application are hereby expressly incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A therapeutic treatment regimen to inhibit development of nucleotide analog chemotherapeutic agent resistance in a cancer susceptible to treatment with a nucleotide analog chemotherapeutic agent comprising:
   a) identifying a subject having a cancer susceptible to treatment with a nucleotide analog chemotherapeutic agent; and
   b) administering an effective amount of at least one nucleotide analog chemotherapeutic agent and either co-administering or subsequently administering an effective amount of a mitotic disruptor/polo-like kinase (Plk) pathway inhibitor comprising ON01910 or a derivative thereof, to the subject.

2. The treatment regimen of claim 1, wherein the nucleotide analog chemotherapeutic agent is selected from the group consisting of cladribine, clofarabine, fludarabine, mercaptopurine, pentostatin, thioguanine, capecitabine, cytarabine, decitabine, fluorouracil, floxuridine, sapacitabine, and gemcitabine.

3. The treatment regimen of claim 1, wherein ON01910 or a derivative thereof is administered at a dose of about 50 mg/m²/week to about 5000 mg/m²/week.

4. The treatment regimen of claim 1, wherein ON01910 or a derivative thereof is administered at least once weekly to three times weekly for two to four weeks.

5. The treatment regimen of claim 1, wherein gemcitabine is administered at a dose of about 500 mg/m²/week to about 1500 mg/m²/week.

6. The treatment regimen of claim 5, wherein gemcitabine is administered at least once weekly to three times weekly for two to four weeks.

7. The treatment regimen of claim 1, wherein the cancer is selected from the group consisting of leukemia and lymphoma, colorectal cancer, pancreatic cancer, lung cancer, breast cancer, ovarian cancer, basal cell carcinoma, bladder cancer, hepatic cancer, prostate cancer, gastric cancer, renal cancer, melanoma, glioma, esophageal cancer, cervical cancer, and myelodysplastic syndromes.

8. The treatment regimen of claim 1, wherein the cancer is pancreatic cancer.

9. The treatment regimen of claim 1, further comprising repeating step b) at least two or more times.

10. A therapeutic treatment regimen to inhibit development of nucleotide analog chemotherapeutic agent resistance in a pancreatic cancer susceptible to treatment with a nucleotide analog chemotherapeutic agent comprising:
    a) identifying a subject having a cancer susceptible to treatment with a nucleotide analog chemotherapeutic agent; and
    b) administering to the subject gemcitabine at a dose of about 1000 mg/m²/week for three weeks and either co-administering or subsequently administering to the subject a mitotic disruptor/polo-like kinase (Plk) pathway inhibitor comprising ON01910 or a derivative thereof, at a dose of about 1800 mg/m²/week for three weeks.

11. The treatment regimen of claim 10, further comprising repeating step b) at least two or more times.

12. A therapeutic treatment regimen to inhibit or reduce nucleotide analog chemotherapeutic agent resistance in a cancer resistant to treatment with a nucleotide analog chemotherapeutic agent comprising:
    a) identifying a subject having a cancer resistant to treatment with a nucleotide analog chemotherapeutic agent; and
    b) administering an effective amount of at least one nucleotide analog chemotherapeutic agent and either co-administering or subsequently administering an effective amount of a mitotic disruptor/polo-like kinase (Plk) pathway inhibitor comprising ON01910 or a derivative thereof, to the subject.

13. The treatment regimen of claim 12, wherein the nucleotide analog chemotherapeutic agent is selected from the group consisting of cladribine, clofarabine, fludarabine, mercaptopurine, pentostatin, thioguanine, capecitabine, cytarabine, decitabine, fluorouracil, floxuridine, sapacitabine, and gemcitabine.

14. The treatment regimen of claim 12, wherein ON01910 or a derivative thereof is administered at a dose of about 50 mg/m$^2$/week to about 5000 mg/m$^2$/week.

15. The treatment regimen of claim 14, wherein ON01910 or a derivative thereof is administered at least once weekly to three times weekly for two to four weeks.

16. The treatment regimen of claim 12, wherein gemcitabine is administered at a dose of about 500 mg/m$^2$/week to about 1500 mg/m$^2$/week.

17. The treatment regimen of claim 16, wherein gemcitabine is administered at least once weekly to three times weekly for two to four weeks.

18. The treatment regimen of claim 12, wherein the cancer is selected from the group consisting of leukemia and lymphoma, colorectal cancer, pancreatic cancer, lung cancer, breast cancer, ovarian cancer, basal cell carcinoma, bladder cancer, hepatic cancer, prostate cancer, gastric cancer, renal cancer, melanoma, glioma, esophageal cancer, cervical cancer, and myelodysplastic syndromes.

19. The treatment regimen of claim 12, wherein the cancer is pancreatic cancer.

20. The treatment regimen of claim 12, further comprising repeating step b) at least two or more times.

* * * * *